United States Patent [19]

Betterton et al.

[11] Patent Number: 5,068,054
[45] Date of Patent: Nov. 26, 1991

[54] FERROELECTRIC LIQUID CRYSTALS

[75] Inventors: Kathleen M. Betterton, San Jose; William D. Hinsberg, Fremont, both of Calif.; Huu T. Nguyen, Pessac, France; Wing T. Tang; Robert J. Twieg, both of San Jose, Calif.

[73] Assignee: International Business Machines Corporation, Armonk, N.Y.

[21] Appl. No.: 322,589

[22] Filed: Mar. 13, 1989

[51] Int. Cl.$^5$ .......................... C09K 19/32; C07C 67/02
[52] U.S. Cl. ........................... 252/299.62; 252/299.01; 252/299.6; 252/299.66; 252/299.67; 558/257; 558/252; 359/103; 359/104
[58] Field of Search ............... 558/257, 252; 252/299.6, 299.61, 299.62, 299.63, 299.64, 299.65, 299.66, 299.67, 299.01; 350/350 R, 350 S

[56] References Cited

U.S. PATENT DOCUMENTS

| | | | |
|---|---|---|---|
| 4,137,250 | 1/1979 | Reynolds | 252/299.6 |
| 4,162,988 | 7/1979 | Maze et al. | 252/299.65 |
| 4,576,732 | 3/1986 | Isogai et al. | 252/299.01 |
| 4,613,209 | 9/1986 | Goodby et al. | 252/299.01 |
| 4,615,586 | 10/1986 | Geary et al. | 252/299.01 |
| 4,653,866 | 3/1987 | Era et al. | 252/299.65 |
| 4,816,178 | 3/1989 | Katagiri et al. | 252/299.01 |
| 4,876,027 | 10/1989 | Yoshinaga et al. | 252/299.6 X |
| 4,906,402 | 3/1990 | Jackson et al. | 252/299.01 X |

FOREIGN PATENT DOCUMENTS

| | | | |
|---|---|---|---|
| 850094 | 3/1990 | European Pat. Off. | 252/299.62 |
| 2603293 | 8/1977 | Fed. Rep. of Germany | 252/299.6 |
| 3629446 | 3/1987 | Fed. Rep. of Germany | 252/299.01 |
| 62-255470 | 11/1987 | Japan | 252/299.01 |
| 63-96152 | 4/1988 | Japan | 252/299.01 |

Primary Examiner—Robert L. Stoll
Assistant Examiner—Richard Treanor
Attorney, Agent, or Firm—Joseph G. Walsh; Robert B. Martin

[57] ABSTRACT

Disclosed are compounds of the general formula:

R—O—Ar—COS—Ph—COO—R' characterized by the presence of the thioester (—COS—) core and wherein R is an alkyl group with typically 8 to 16 carbon atoms, Ar is a substituted aromatic core group such as 1,4-benzene, 2,6-naphthalene, 4,4'-biphenyl, or 4,4'-diphenylethane, and R' is a chiral branched alkyl group such as the 1-substituted cases 1-methylpropyl through 1-methyloctyl or 2-substituted case such as 2-methylbutyl. These materials or their mixtures possess ferroelectric phases and as such are of interest for electro-optical applications. In certain cases specific materials are of particular interest due to the existence of stable ferroelectric phases near room temperature with large polarization density and fast electro-optic response.

5 Claims, 1 Drawing Sheet

FERROELECTRIC LIQUID CRYSTALS

TECHNICAL FIELD

The present invention is concerned with ferroelectric liquid crystal compounds having a specified structure. The compounds are useful, for example, for electro-optical modulation in light shutters or flat panel displays.

BACKGROUND OF THE INVENTION

Liquid crystalline materials have come to be widely used as the active element in electronic devices which modulate the properties of light. The performance of these devices is in large part determined by the properties of the liquid crystal material. Nematic liquid crystals have been most widely utilized at this time, being used for the construction of several different forms of twisted-nematic type display devices such as are used for wrist watches, small computers and the like. Such displays are limited in response time by the nature of the nematic liquid crystalline phase and by the extent to which the structure of that phase must be perturbed to produce a useful optical response.

It has been demonstrated that liquid crystals possessing a ferroelectric phase can be utilized to fabricate useful electro-optic devices which exhibit response speeds far exceeding those attained to date with nematic liquid crystal materials (Clark and Lagerwall, Appl. Phys. Lett., 36, 899 (1980)). The present invention relates to a group of liquid crystalline materials which possess ferroelectric phases as pure materials, as mixtures with each other and as mixtures in smectic hosts. Such materials and mixtures are of use for electro-optical modulation in light shutters, flat panel displays and the like.

There are a host of critical material properties which must be fulfilled for application of such materials in a practical device. Among these critical requirements are the following:

1) Stable ferroelectric phase, particularly the $S_c^*$ phase, at or near ambient temperature. Although an enantiotropic phase is preferred, materials with monotropic ferroelectric phases, and even monomers which of themselves have no ferroelectric phase are still of use in appropriate mixtures.

2) Large spontaneous polarization to provide efficient coupling of the external applied field to the ferroelectric liquid crystal contained in the device.

3) Fast electro-optical response to an applied electric field, especially in electronic display devices where a high degree of signal multiplexing exists.

It is the object of this invention to provide ferroelectric liquid crystal materials and compositions which satisfy these requirements.

BACKGROUND ART

The prior art describes a large variety of ferroelectric liquid crystals with many combinations of core and chiral tail combinations. However, relatively few of these materials contain the thioester core in spite of its propensity to improve the thermodynamic stability of the requisite ferroelectric phases.

The German patent FRG 2,603,293 (1977) assigned to Krause of Merck describes a variety of thioester core smectic liquid crystals. None of these is ferroelectric and none contains a structural unit formally derived from 4-mercaptobenzoic acid. U.S. Pat. No. 4,162,988 (1979), assigned to Maze and Oppenheim of Motorola Inc., describes biphenyl thioester liquid crystals but none which is ferroelectric. U.S. Pat. No. 4,424,372 (1984) assigned to Hsu, et al. of Timex Corp. describes thioester core nematic liquid crystals. Again in this case none of the subject materials is ferroelectric. Ferroelectric liquid crystals containing chiral ester side chains are described in U.S. Pat. No. 4,576,732 (1986) assigned to Isogai, et al. of Hitachi, Ltd. but none contains the valuable thioester core. U.S. Pat. No. 4,653,866 (1987) assigned to Era, et. al. of Hitachi, Ltd. describes thioester core smectic liquid crystals but none which is ferroelectric. The materials in this instance are intended for light scattering types of displays.

The publication by Nguyen and coworkers (Nguyen Huu Tinh, C. Salleneuve, A. Babeau, A. Robineau, C. Destrade, Mol. Cryst. Liq. Cryst. Lett., Vol 4, 93, (1987)) describes thioester core FLC's with chiral ether tails. Here both the chiral and achiral tails are joined to the thioester core through aryl ether linkages and the compounds described exhibit low spontaneous polarizations. The paper by Twieg et al. (R. J. Twieg, K. Betterton, Nguyen Huu Tinh, W. Tang, W. Hinsberg, Ferroelectrics, in press (1989)), describes a series of thioester core FLC's containing chlorinated chiral side chains which exhibit large spontaneous polarization and fast electro-optic response but whose stable ferroelectric phases occur in a temperature range far above ambient.

DISCLOSURE OF THE INVENTION

The present invention is concerned with compounds of the general formula: R—O—Ar—CO-S—Ph—COO—R' characterized by the presence of the thioester (—COS—) core and wherein R is an alkyl group with typically 8 to 16 carbon atoms, Ar is a substituted aromatic core group such as 1,4-benzene, 2,6-naphthalene, 4,4'-biphenyl, or 4,4'-diphenylethane, and R' is a chiral branched alkyl group such as the 1-substituted cases 1-methylpropyl through 1-methyloctyl or 2-substituted case such as 2-methylbutyl. These materials or their mixtures possess ferroelectric phases and as such are of interest for electro-optical applications. In certain cases specific materials are of particular interest due to the existence of stable ferroelectric phases near room temperature with large polarization density and fast electro-optic response.

The invention is now illustrated in more detail by the following examples. However, these examples are not to limit the scope of the present invention. The values quoted for the ferroelectric ranges and values of the polarization are subject to chemical and enantiomeric purity of the materials as well as the heating rates, surface treatment and other parameters of the characterization cells.

The synthesis of these ferroelectric liquid crystals is accomplished in three steps in most cases, as is outlined in the accompanying drawing.

Figure 1:
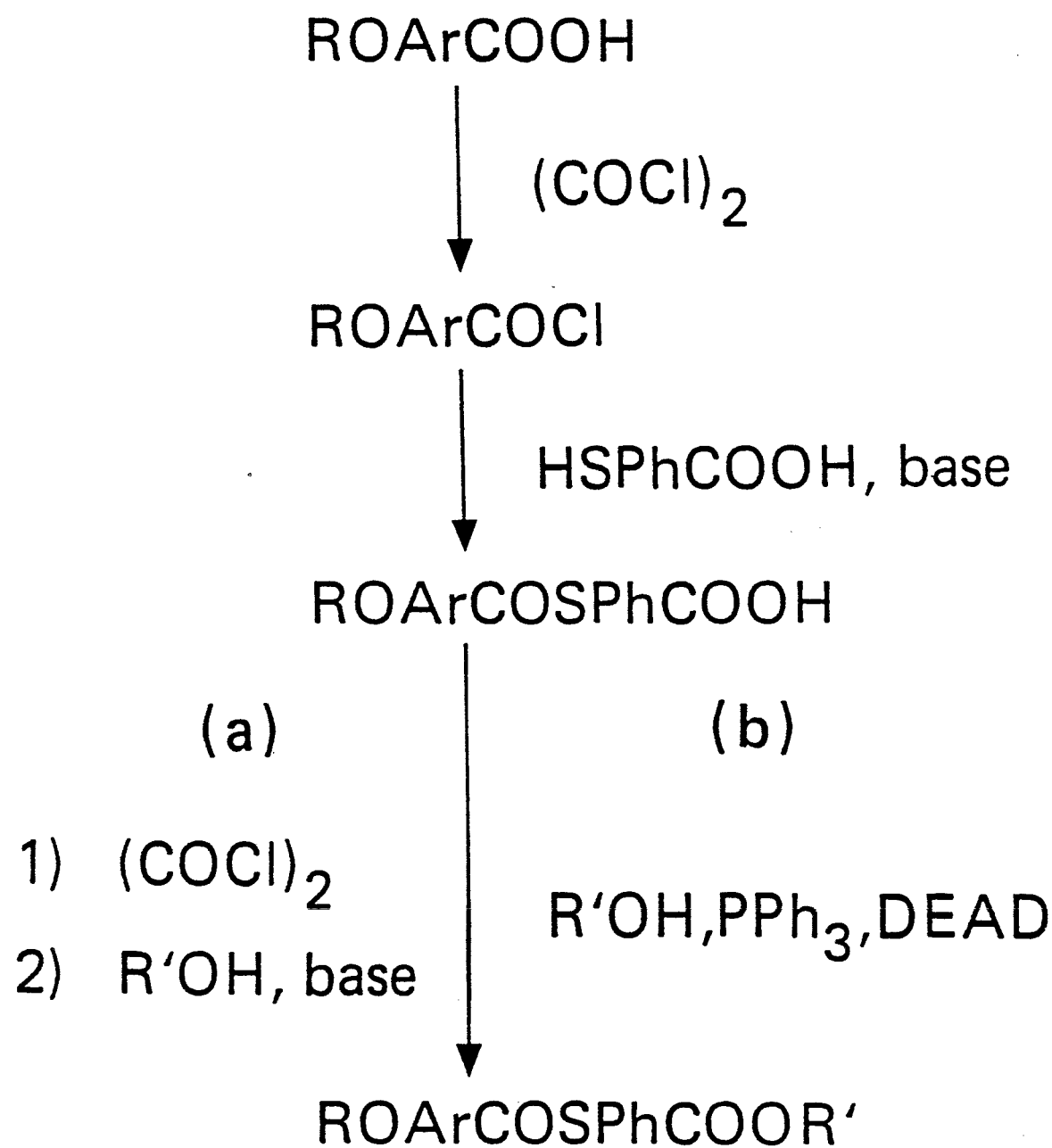
FIG. 1 is a schematic outline of the synthetic routes useful in making the compounds of the present inventions.

First, the alkoxy aromatic acid RO—Ar—COOH is converted to its acid chloride RO—Ar—COCl which in turn is reacted with 4-mercaptobenzoic acid HSPhCOOH in the presence of base to provide the carboxylic acid functionalized intermediate RO—Ar—COS—PhCOOH. This carboxylic acid intermediate is then esterified by reaction with a chiral alcohol. Two different esterification methods have been found effective: A conversion of the acid to the acid chloride RO—Ar—COS—PhCOCl and coupling with R'OH in the presence of base, or B direct reaction of the carboxylic acid with the alcohol R'OH by a modification of the procedure of Mitsonobu (S. Bittner an Y. Assaf, Chemistry and Industry (London), 281 (1975)). In either case the product RO—Ar—CO-S—Ph—COO—R' is obtained. When R'OH is a chiral secondary alcohol the esterification proceeds with retention of configuration in the acid chloride method and with inversion in the Mitsonobu technique. The examples provided are illustrative.

Examples of Typical Preparations

Preparation of the intermediate acid:

4-(4'-n-dodecyloxybenzoylthioxy)benzoic acid
R—O—Ar—COS—Ph—COO—R'
R=$C_{12}H_{25}$, Ar=1,4-Ph,R'=H A solution of 4-n-dodecyloxybenzoylchloride (9.76 g, 30 mmol, obtained from the corresponding acid and oxalyl chloride) in methylene chloride (50 ml) was added dropwise over one hour to a stirred solution of 4-mercaptobenzoic acid (4.7 g, 30 mmol) and triethylamine (3.0 g, 30 mmol) in dichloromethane (150 ml) in an ice bath. The resulting solution was stirred overnight at room temperature and evaporated to dryness. The residue was drowned with dilute aqueous hydrochloric acid and the product isolated by suction filtration, washed with water and air dried. After recrystallization from acetic acid there was obtained the product (9.2 g, 69%) as a cream colored solid: mp K135$S_c$210N229I.

The preparation of the naphthalene, biphenyl, and diphenylethane containing carboxylic acid analogs is similar except the appropriate acid chloride is substituted for the dodecyloxybenzoylchloride.

Preparation of the liquid crystal:

a) Acid chloride method (retention of configuration)
1-(S)-methylheptyl-4-(4'-n-dodecyloxybenzothioxy) benzoate
R—O—Ar—COS—Ph—COO—R'
R=$C_{12}H_{25}$, Ar=1,4-Ph,R'=CH($CH_3$)($CH_2$)$_6$H To a solution of the carboxylic acid chloride 4-(4'-n-dodecyloxybenzothioxy) benzoyl chloride (460 mg, 1 mmol, obtained from the acid and excess oxalyl chloride) and (S)-2-octanol (120 mg, 1.0 mmol) in dichloromethane (10 ml) was added dropwise triethylamine (0.10 g, 1.0 mmol) and the resulting solution was stirred overnight at room temperature. The reaction was concentrated by rotary evaporation, extracted with ethyl ether, and dried over anhydrous sodium sulfate. After filtration and evaporation the residue was chromatographed on silica gel with toluene and crystallized from ethanol. Yield 0.13 g, mp K36$S_c$* 38 $S_A$42 I.

b) Mitsonobu method (inversion of configuration)

1-(S)-methylpropyl-4-(4'-n-tetradecyloxybenzothioxy) benzoate
R—O—Ar—COS—PH—COO—R'
R=$C_{12}H$ Ar=1,4-Ph,R'=CH($CH_3$)($CH_2$)$_2$H In a 100 ml round bottom flask with stir bar was placed the carboxylic acid 4—(4'-n-tetradecyloxybenzoylthioxy)-benzoic acid, (1.3 g, 2.76 mmol), R-(-)-2-butanol (306 mg, 3.03 mmol), triphenylphosphine (1.02 g, 3.9 mmol) and anhydrous tetrahydrofuran (20 ml). The resulting solution was stirred in a water bath and diethylazodicarboxylate (DEAD) (681 mg, 3.9 mmol) was added dropwise over one minute. The resulting solution was stirred for 30 minutes and then silica gel was added and the slurry evaporated to dryness. The adsorbed material was placed at the top of a silica gel column and eluted with toluene, the fractions containing the pure product were combined, concentrated and finally recrystallized from ethanol. Yield 1.14 g: mp K 56.4$S_c$*(39.8) SA64I.

Preparation of the other materials with different chiral tails, different cores and achiral tail lengths was carried out in an analogous fashion using the acid chloride esterification or the Mitsonobu esterification.

Mesomorphic and Ferroelectric Properties

The most convenient and relevant assay to determine the existence and properties of a ferroelectric phase is the polarization measurement for which the methodology has been described in the literature (see, for example, Miyasato, et. al., Jpn. J. Appl. Phys., 22, L661 (1983)). Here the candidate material in its isotropic phase is loaded by capillary action into a cell made from two pieces of glass separated by about 25 μm,. with a lithographically defined capacitor structure ½ inch in diameter etched into the conducting ITO surface. The cell is kept in a temperature controlled sample holder and gradually cooled from the isotropic state while a triangular voltage modulation is applied. The existence of a ferroelectric phase is manifested by the appearance of a response current from which the polarization $P_S$ can be calculated at a given temperature. The sample is gradually cooled until the polarization current disappears due to crystallization or entry into an adjacent non-ferroelectric phase. The onset temperature (if any), breadth and polarization of the ferroelectric phase is strongly dependent on the exact structure of the candidate material. Here the onset temperature and disappearance temperature (in °C.) for the $S_c$* phase is given. A polarization value (absolute value in nC/cm$^2$) is also provided usually at 10° below the $S_c$* onset at $T_c$.

TABLE

FERROELECTRIC RANGES AND ABSOLUTE POLARIZATION FOR COMPOUNDS WITH THE STRUCTURE
H(CH$_2$)$_n$OArCOSPhCOOC*H(CH$_3$)(CH$_2$)$_{m-2}$H

| n | m | $S_c$* range (°C.) | $T_c$-T | $P_s$ (nC/cm$^2$) |
|---|---|---|---|---|
| Ar = 1,4-Ph | | | | |
| 12 | 9 | 26-12 | (10) | 86 |
| 8 | 8 | no $S_c$* found | | |
| 9 | 8 | 29 | very weak monotropic phase | |
| 10 | 8 | 34-30 | (4) | 81 |
| 11 | 8 | 33-20 | (10) | 112 |
| 12 | 8 | 37-20 | (10) | 118 |
| 13 | 8 | 35-26 | (9) | 107 |
| 14 | 8 | 37-27 | (10) | 105 |
| 14 | 8 | 39-20 | (10) | 114 |
| 12 | 8 | | | (1:1 mixture) |
| 13 | 8 | 32-15 | (10) | 112 |
| 11 | 8 | | | (1:1 mixture) |
| 15 | 8 | 39-26 | (10) | 43 |
| 16 | 8 | 29 | weak monotropic phase | |
| 12 | 7 | 38-24 | (10) | 113 |
| 10 | 6 | 38-29 | very complicated polarization properties | |
| 12 | 6 | 34 | weak monotropic phase | |
| 14 | 6 | 39 | weak monotropic phase | |
| 15 | 6 | 39-32 | (3) | 33 |
| 12 | 5 | 67-51 | (10) | 94 |
| 10 | 4 | 45-30 | (10) | 28 |
| 12 | 4 | 43-20 | (10) | 28 |
| 14 | 4 | 41-27 | (10) | 21 |
| 15 | 4 | 38-35 | (2) | 6 |
| 16 | 4 | 35-32 | (3) | 9 |

TABLE-continued

FERROELECTRIC RANGES AND ABSOLUTE POLARIZATION FOR COMPOUNDS WITH THE STRUCTURE
$H(CH_2)_n OArCOSPhCOOC^*H(CH_3)(CH_2)_{m-2}H$

| n | m | $S_c^*$ range (°C.) | $T_c$-T | $P_s$ (nC/cm$^2$) |
|---|---|---|---|---|
| 12 | | 56–44 | (8) | 4 |
| Ar = 2,6-naphthalene | | | | |
| 10 | 8 | 73–67 | (2) | 25 |
| Ar = 4,4'-biphenyl | | | | |
| 8 | 8 | 148–128 | (10) | 77 |
| Ar = 4,4'-diphenylethane | | | | |
| 10 | 8 | 104–81 | (10) | 80 | chiral tail from (S)-2-methyl-1-butanol

The electro-optical behavior of the liquid crystal or liquid crystalline mixture is of key importance for applications requiring light modulation. For the subject materials this was assessed using the following procedure. An optical switching cell was prepared from two glass plates bearing transparent conducting electrode patterns formed of indium tin oxide, and upon which was placed a thin, mechanically rubbed coating of a nylon polymer known to promote uniform alignment of liquid crystalline phases. The spacing between the plates was maintained in the range of 1–2 μm. The subject liquid crystalline material was placed between these plates, a periodic square wave potential of +−15 volts/μm was applied across the cell in the manner known to induce reorientation of liquid crystals in an aligned, surface-stabilized ferroelectric liquid crystal geometry. The optical response resulting from this reorientation was assessed by observing through crossed polarizers the intensity modulation of a light beam, such as that of a low-power helium neon laser, passing through the cell. A typical electro-optical response characterized as the change in cell transmittance versus time for a 1:1 mixture of $H(CH_2)_{12}OPhCOSPhCOOC^*H(CH_3)(CH_2)_6H$ and $H(CH_2)_{14}OPhCOSPhCOOC^*H(CH_3)(CH_2)_6H$ was below 30 microseconds over the available ferroelectric range of the mixture. The response time as used here is defined as the period required for the optical transmittance to change from 0 to 100% of the total range achievable for a given liquid crystalline material and a particular cell and optical configuration upon rapid reversal in polarity of the applied voltage.

What is claimed is:

1. A ferroelectric liquid crystal of the formula: $H(CH_2)_n OArCOSPhCOOC^*H(CH_3)(CH_2)_{m-2}H$ where n is in the range 8–16, m is in the range 4–8, is selected from the group consisting of 2,6-naphthyl, 4,4'-biphenyl, and 4,4'-diphenylethane, and Ph is 1,4-phenylene.

2. A ferroelectric liquid crystal compound as claimed in claim 1 where n=10, m=8 and Ar=2,6-naphthyl.

3. A ferroelectric liquid crystal compound as claimed in claim 1 where n=8, m=8 and Ar=4,4'-biphenyl.

4. A ferroelectric liquid crystal compound as claimed in claim 1 where n=10, m=8 and Ar=4,4'-diphenylethane.

5. A ferroelectric liquid crystal composition comprising a mixture of liquid crystalline compounds, comprising at least one compound as claimed in claim 1.

* * * * *